(12) United States Patent
Gross

(10) Patent No.: US 8,923,972 B2
(45) Date of Patent: Dec. 30, 2014

(54) ELLIPTICAL ELEMENT FOR BLOOD PRESSURE REDUCTION

(75) Inventor: Yossi Gross, Moshav Mazor (IL)

(73) Assignee: Vascular Dynamics, Inc., Mountain View, CA (US)

(*) Notice: Subject to any disclaimer, the term of this patent is extended or adjusted under 35 U.S.C. 154(b) by 1732 days.

(21) Appl. No.: 11/881,256

(22) Filed: Jul. 25, 2007

(65) Prior Publication Data

US 2008/0033501 A1   Feb. 7, 2008

Related U.S. Application Data

(63) Continuation-in-part of application No. PCT/IL2006/000856, filed on Jul. 25, 2006.

(60) Provisional application No. 60/702,491, filed on Jul. 25, 2005, provisional application No. 60/721,728, filed on Sep. 28, 2005.

(51) Int. Cl.
| | | |
|---|---|---|
| *A61N 1/05* | (2006.01) | |
| *A61F 2/82* | (2013.01) | |
| *A61N 1/32* | (2006.01) | |
| *A61N 1/36* | (2006.01) | |
| *A61F 2/856* | (2013.01) | |
| *A61F 2/06* | (2013.01) | |

(52) U.S. Cl.
CPC . *A61F 2/82* (2013.01); *A61N 1/326* (2013.01); *A61N 1/36017* (2013.01); *A61N 1/36117* (2013.01); *A61F 2/856* (2013.01); *A61F 2002/065* (2013.01); *A61F 2250/0001* (2013.01); *A61N 1/056* (2013.01)
USPC .............. 607/44; 623/1.15; 623/1.16

(58) Field of Classification Search
CPC .............. A61N 1/326; A61N 1/056
USPC .............. 607/44; 623/1.1, 1.15
See application file for complete search history.

(56) References Cited

U.S. PATENT DOCUMENTS

| | | |
|---|---|---|
| 3,650,277 A | 3/1972 | Sjostrand et al. |
| 4,201,219 A | 5/1980 | Bozal |
| 4,791,931 A | 12/1988 | Slate |

(Continued)

FOREIGN PATENT DOCUMENTS

| | | |
|---|---|---|
| EP | 0791341 | 8/1997 |
| EP | 1 127 557 | 8/2001 |

(Continued)

OTHER PUBLICATIONS

B. Ziaie, et al., "An Implantable Pressure Sensor Cuff for Tonometric Blood Pressure Measurement," IEEE Solid-State Sensor and Actuator Workshop, pp. 216-219, Jun. 1998.

(Continued)

*Primary Examiner* — Carl H Layno
*Assistant Examiner* — Jennifer Ghand
(74) *Attorney, Agent, or Firm* — Wilson Sonsini Goodrich & Rosati

(57) ABSTRACT

Apparatus is provided for treating hypertension of a subject. The apparatus includes an implantable element which has a non-circular shape and which is configured to reduce the hypertension by facilitating an assumption of a non-circular shape by a blood vessel in a vicinity of a baroreceptor of the subject, during diastole of the subject. Other embodiments are also described.

9 Claims, 3 Drawing Sheets

(56) References Cited

U.S. PATENT DOCUMENTS

| | | |
|---|---|---|
| 4,830,003 A | 5/1989 | Wolff |
| 4,938,766 A | 7/1990 | Jarvik |
| 5,403,341 A | 4/1995 | Solar |
| 5,437,285 A | 8/1995 | Verrier |
| 5,458,626 A | 10/1995 | Krause |
| 5,630,829 A | 5/1997 | Lauterjung |
| 5,669,924 A | 9/1997 | Shaknovich |
| 5,707,400 A | 1/1998 | Terry, Jr. et al. |
| 5,727,558 A | 3/1998 | Hakki |
| 6,086,527 A | 7/2000 | Talpade |
| 6,306,141 B1 | 10/2001 | Jervis |
| 6,322,553 B1 | 11/2001 | Vito |
| 6,375,666 B1 | 4/2002 | Mische |
| 6,413,273 B1 | 7/2002 | Baum |
| 6,442,424 B1 | 8/2002 | Ben-Haim |
| 6,522,926 B1 | 2/2003 | Kieval |
| 6,554,856 B1 | 4/2003 | Doorly et al. |
| 6,575,994 B1 | 6/2003 | Marin et al. |
| 6,616,624 B1 | 9/2003 | Kieval |
| 6,641,605 B1 | 11/2003 | Stergiopulos |
| 6,669,686 B1 | 12/2003 | Singh |
| 6,681,136 B2 | 1/2004 | Schuler |
| 6,764,498 B2 | 7/2004 | Mische |
| 6,850,801 B2 | 2/2005 | Kieval |
| 6,899,669 B2 | 5/2005 | Vito |
| 6,957,106 B2 | 10/2005 | Schuler |
| 6,972,031 B1 | 12/2005 | Braginsky et al. |
| 6,974,445 B2 | 12/2005 | Stergiopulos |
| 6,985,774 B2 | 1/2006 | Kieval |
| 7,008,446 B1 | 3/2006 | Amis et al. |
| 7,044,981 B2 | 5/2006 | Liu et al. |
| 7,060,080 B2 | 6/2006 | Bachman |
| 7,094,254 B2 | 8/2006 | Stergiopulos |
| 7,128,750 B1 | 10/2006 | Stergiopulos |
| 7,158,832 B2 | 1/2007 | Kieval |
| 7,159,593 B2 | 1/2007 | McCarthy et al. |
| 7,194,313 B2 | 3/2007 | Libbus |
| 7,201,772 B2 | 4/2007 | Schwammenthal |
| 7,218,964 B2 | 5/2007 | Hill et al. |
| 7,238,191 B2 | 7/2007 | Bachmann |
| 7,270,675 B2 | 9/2007 | Chun |
| 7,300,449 B2 | 11/2007 | Mische |
| 7,373,204 B2 | 5/2008 | Gelfand et al. |
| 7,381,222 B2 | 6/2008 | Pflueger et al. |
| 7,389,149 B2 | 6/2008 | Rossing |
| 7,395,119 B2 | 7/2008 | Hagen |
| 7,491,229 B2 | 2/2009 | Eder |
| 7,530,995 B2 | 5/2009 | Quijano et al. |
| 7,625,400 B2 | 12/2009 | Bowe |
| 7,628,803 B2 | 12/2009 | Pavcnik et al. |
| 7,637,937 B2 | 12/2009 | Case et al. |
| 7,647,931 B2 | 1/2010 | Pflueger |
| 8,361,140 B2 | 1/2013 | Meyer et al. |
| 2001/0003801 A1* | 6/2001 | Strecker .............. 623/1.11 |
| 2002/0173838 A1 | 11/2002 | Frazier |
| 2003/0060585 A1 | 3/2003 | Radhakrishnan et al. |
| 2003/0060858 A1 | 3/2003 | Kieval et al. |
| 2003/0199806 A1 | 10/2003 | Kieval |
| 2004/0010303 A1 | 1/2004 | Bolea |
| 2004/0019364 A1 | 1/2004 | Kieval |
| 2004/0106976 A1 | 6/2004 | Bailey et al. |
| 2004/0111006 A1* | 6/2004 | Alferness et al. .......... 600/16 |
| 2004/0193092 A1 | 9/2004 | Deal |
| 2004/0249442 A1 | 12/2004 | Fleming, III et al. |
| 2004/0254616 A1 | 12/2004 | Rossing |
| 2005/0027346 A1 | 2/2005 | Arkusz et al. |
| 2005/0033407 A1 | 2/2005 | Weber et al. |
| 2005/0090894 A1 | 4/2005 | Pazienza et al. |
| 2005/0096710 A1 | 5/2005 | Kieval |
| 2005/0143765 A1 | 6/2005 | Bachman |
| 2005/0143766 A1 | 6/2005 | Bachman |
| 2005/0143785 A1 | 6/2005 | Libbus |
| 2005/0149128 A1 | 7/2005 | Heil, Jr. |
| 2005/0149131 A1 | 7/2005 | Libbus |
| 2005/0149143 A1 | 7/2005 | Libbus |
| 2005/0154418 A1 | 7/2005 | Kieval et al. |
| 2005/0203610 A1 | 9/2005 | Tzeng |
| 2005/0232965 A1 | 10/2005 | Falotico |
| 2005/0251212 A1 | 11/2005 | Kieval |
| 2005/0261257 A1 | 11/2005 | Vermeer |
| 2006/0004417 A1 | 1/2006 | Rossing |
| 2006/0004420 A1 | 1/2006 | Rossing |
| 2006/0004430 A1 | 1/2006 | Rossing |
| 2006/0074453 A1 | 4/2006 | Kieval et al. |
| 2006/0089678 A1 | 4/2006 | Shalev |
| 2006/0111626 A1 | 5/2006 | Rossing |
| 2006/0217588 A1* | 9/2006 | Gross et al. .............. 600/16 |
| 2006/0241334 A1 | 10/2006 | Dubi |
| 2006/0265038 A1 | 11/2006 | Hagen |
| 2006/0276852 A1 | 12/2006 | Demarais |
| 2006/0293712 A1 | 12/2006 | Kieval |
| 2007/0021790 A1 | 1/2007 | Kieval |
| 2007/0021792 A1 | 1/2007 | Kieval |
| 2007/0021794 A1 | 1/2007 | Kieval |
| 2007/0021796 A1 | 1/2007 | Kieval |
| 2007/0021797 A1 | 1/2007 | Kieval |
| 2007/0021798 A1 | 1/2007 | Kieval |
| 2007/0021799 A1 | 1/2007 | Kieval |
| 2007/0038255 A1 | 2/2007 | Kieval |
| 2007/0038259 A1 | 2/2007 | Kieval |
| 2007/0038260 A1 | 2/2007 | Kieval |
| 2007/0038261 A1 | 2/2007 | Kieval |
| 2007/0038262 A1 | 2/2007 | Kieval |
| 2007/0049989 A1 | 3/2007 | Rossing |
| 2007/0055296 A1 | 3/2007 | Stergiopulos |
| 2007/0060972 A1 | 3/2007 | Kieval |
| 2007/0100433 A1 | 5/2007 | Limon |
| 2007/0106340 A1 | 5/2007 | Bolea |
| 2007/0142870 A1 | 6/2007 | Greenberg |
| 2007/0156167 A1* | 7/2007 | Connors et al. ............ 606/194 |
| 2007/0156198 A1 | 7/2007 | Rossing |
| 2007/0156201 A1 | 7/2007 | Rossing |
| 2007/0167984 A1 | 7/2007 | Kieval |
| 2007/0185542 A1 | 8/2007 | Bolea |
| 2007/0185543 A1 | 8/2007 | Rossing |
| 2007/0187255 A1 | 8/2007 | Ogasawara |
| 2007/0198082 A1 | 8/2007 | Kapadia et al. |
| 2007/0250085 A1 | 10/2007 | Bachman |
| 2007/0276442 A1 | 11/2007 | Hagen |
| 2007/0276459 A1 | 11/2007 | Rossing |
| 2007/0282385 A1 | 12/2007 | Rossing |
| 2008/0004673 A1 | 1/2008 | Rossing |
| 2008/0009916 A1 | 1/2008 | Rossing |
| 2008/0009917 A1 | 1/2008 | Rossing |
| 2008/0027469 A1 | 1/2008 | Bachman |
| 2008/0033501 A1 | 2/2008 | Gross |
| 2008/0046054 A1 | 2/2008 | Hjelle |
| 2008/0051767 A1 | 2/2008 | Rossing |
| 2008/0082137 A1 | 4/2008 | Kieval |
| 2008/0097540 A1 | 4/2008 | Bolea |
| 2008/0114439 A1 | 5/2008 | Ramaiah |
| 2008/0132966 A1 | 6/2008 | Levin |
| 2008/0140167 A1 | 6/2008 | Hagen et al. |
| 2008/0154349 A1 | 6/2008 | Rossing |
| 2008/0161865 A1 | 7/2008 | Hagen |
| 2008/0161887 A1 | 7/2008 | Hagen |
| 2008/0167690 A1 | 7/2008 | Cody |
| 2008/0167693 A1 | 7/2008 | Kieval |
| 2008/0167694 A1 | 7/2008 | Bolea |
| 2008/0167696 A1 | 7/2008 | Cates |
| 2008/0167699 A1 | 7/2008 | Kieval |
| 2008/0171923 A1 | 7/2008 | Bolea |
| 2008/0172101 A1 | 7/2008 | Bolea |
| 2008/0172104 A1 | 7/2008 | Kieval |
| 2008/0181927 A1 | 7/2008 | Zhao |
| 2008/0194905 A1 | 8/2008 | Walsh |
| 2008/0195190 A1 | 8/2008 | Bland et al. |
| 2008/0275539 A1 | 11/2008 | Williams et al. |
| 2008/0319504 A1 | 12/2008 | Loushin |
| 2009/0248138 A1 | 10/2009 | Golesworthy |
| 2009/0248141 A1 | 10/2009 | Shandas et al. |
| 2009/0264914 A1 | 10/2009 | Riina |
| 2009/0292348 A1 | 11/2009 | Berez et al. |
| 2009/0306756 A1 | 12/2009 | Cho |

(56) References Cited

U.S. PATENT DOCUMENTS

| | | |
|---|---|---|
| 2010/0211131 A1 | 8/2010 | Williams |
| 2011/0077729 A1 | 3/2011 | Gross et al. |
| 2011/0178416 A1 | 7/2011 | Gross et al. |
| 2011/0213408 A1 | 9/2011 | Gross et al. |
| 2011/0230953 A1 | 9/2011 | Gross |
| 2013/0172981 A1 | 7/2013 | Gross et al. |

FOREIGN PATENT DOCUMENTS

| | | |
|---|---|---|
| EP | 1 153 581 | 11/2001 |
| EP | 1 200 152 | 5/2002 |
| EP | 1 234 554 | 8/2002 |
| EP | 1 343 112 | 9/2003 |
| EP | 1483730 B1 | 10/2005 |
| WO | WO 01/05463 | 1/2001 |
| WO | WO 01/85063 | 11/2001 |
| WO | WO 02/26314 | 4/2002 |
| WO | WO 03/076008 | 9/2003 |
| WO | WO 03/077191 | 9/2003 |
| WO | 2003082080 A3 | 10/2003 |
| WO | WO 03/082080 | 10/2003 |
| WO | WO 03/082403 | 10/2003 |
| WO | 2004073484 A3 | 9/2004 |
| WO | WO 2004/073484 | 9/2004 |
| WO | WO2005021063 | 3/2005 |
| WO | 2005065771 A1 | 7/2005 |
| WO | 2005084389 A2 | 9/2005 |
| WO | WO 2005/084389 | 9/2005 |
| WO | 2005097256 A3 | 10/2005 |
| WO | WO 2005/097256 | 10/2005 |
| WO | 2006012033 A3 | 2/2006 |
| WO | 2006012050 A3 | 2/2006 |
| WO | WO 2006/012033 | 2/2006 |
| WO | WO 2006/012050 | 2/2006 |
| WO | WO 2006/032902 | 3/2006 |
| WO | 2006041664 A3 | 4/2006 |
| WO | 2006042280 A2 | 4/2006 |
| WO | 2006042280 A3 | 4/2006 |
| WO | WO 2006/040647 | 4/2006 |
| WO | WO 2006/041664 | 4/2006 |
| WO | 2006125163 A2 | 11/2006 |
| WO | WO 2006/125163 | 11/2006 |
| WO | 2007013065 A3 | 2/2007 |
| WO | WO 2007/013065 | 2/2007 |
| WO | 2007047152 A3 | 4/2007 |
| WO | WO 2007/047152 | 4/2007 |
| WO | 2007080595 A3 | 7/2007 |
| WO | WO 2007/080595 | 7/2007 |
| WO | 2007114860 A3 | 10/2007 |
| WO | 2007118090 A2 | 10/2007 |
| WO | WO 2007/114860 | 10/2007 |
| WO | WO 2007/118090 | 10/2007 |
| WO | 2007136850 A2 | 11/2007 |
| WO | 2007136851 A2 | 11/2007 |
| WO | WO 2007/136850 | 11/2007 |
| WO | WO 2007/136851 | 11/2007 |
| WO | 2008039982 A2 | 4/2008 |
| WO | WO 2008/039982 | 4/2008 |
| WO | 2008083120 A2 | 7/2008 |
| WO | 2008083235 A2 | 7/2008 |
| WO | 2008083235 A3 | 7/2008 |
| WO | WO 2008/083120 | 7/2008 |
| WO | WO 2008/083235 | 7/2008 |
| WO | WO 2009/018394 | 2/2009 |
| WO | 2010035271 A1 | 4/2010 |
| WO | 2011089601 A1 | 7/2011 |

OTHER PUBLICATIONS

"Ascorbic Acid Selectively Improves Large Elastic Artery Compliance in Postmenopausal Women," Moreau K.L., Hypertension 2005;45: 1107.

"Carotid sinus nerve blockade to reduce blood pressure instability following carotid endarterectomy: a systematic review and meta-analysis," Tang T.Y., Eur J Vasc Endovasc Surg. Sep. 2007; 34(3):304-11, (an abstract).

"Coronary artery baroreceptor-mediated changes in arterial pressure: a pilot study in conscious and anaesthetized sheep," Bennetts J.S., Clin Exp Pharmacol Physiol. Sep. 2001; 28(9):768-72, (an abstract).

"Effect of increased renal venous pressure on renal function," Doty J. M., The Journal of Trauma: Injury, Infection, and Critical Care: Dec. 1999, vol. 47, Issue 6, p. 1000, (an abstract).

"Glomerular ultrafiltration dynamics during increased renal venous pressure," J.R. Dilley, AJP—Renal Physiology, vol. 244, Issue 6 650-F658, (an abstract).

"Implantable penile venous compression device: initial experience in the acute canine model," Paick J., The Journal of Urology 1992, vol. 148, No. 1, pp. 188-191, (an abstract).

"Theoretical and electrophysiological evidence for axial loading about aortic baroreceptor nerve terminals in rats," Feng B, Am J Physiol Heart Circ Physiol. Dec. 2007; 293(6):H3659-72.

"The effects of altering mean pressure, pulse pressure and pulse frequency on the impulse activity in baroreceptor fibres from the aortic arch and right subclavian artery in the rabbit," Angell James JE, J Physiol. Apr. 1971; 214(1):65-88.

International search report and written opinion dated Jan. 24, 2007 for PCT/IL2006/000856.

U.S. Appl. No. 60/702,491.

U.S. Appl. No. 60/721,728.

S. Levenberg, et al., "Endothelial cells derived from human embryonic stem cells", PNAS Apr. 2, 2002, vol. 99, No. 7 pp. 4391-4396.

J.H.P. Lardenoye, et al., "Inhibition of Accelerated Atherosclerosis in Vein Grafts by Placement of External Stent in ApoE*3-Leiden Transgenic Mice", Arteriosclerosis, Thrombosis, and Vascular Biology. 2002; 22:1433.) © 2002.

An International Search Report dated Feb. 3, 2010, which issued during the prosecution of Applicant's PCT/IL09/00932.

Mendelsohn (1998) Am J Cardiol 82:1077-1081.

Riley, W. A., Barnes, R. W., Evans, G W, Burke, G L, Evans, Gregory W, & Burke, Gregory L. (1992). Ultrasonic measurement of the elastic modulus of the common carotid artery. The Atherosclerosis Risk in Communities (ARIC) Study WA Riley, RW Barnes, GW Evans and GL Burke Stroke 1992;23;952-956. Stroke.

Delfino, A., Stergiopulos, N., & Moore, J. E. (1997) Residual Strain Effects on the Stress Field in a Thick Wall Finite Element Model of the Human Carotid Bifurcation. Science, 30(8), 777-786.

Mendelowitz, D., & Scher, A M. (1990). Pulsatile pressure can prevent rapid baroreflex resetting. The American journal of physiology, 258(1 Pt 2), H92-100. Retrieved from http://www.ncbi.nlm.nih.gov/pubmed/2301618.

An Office Action dated Mar. 14, 2013, which issued during the prosecution of U.S. Appl. No. 13/030,384.

An Office Action dated Sep. 27, 2012, which issued during the prosecution of U.S. Appl. No. 13/030,384.

An Office Action dated Jan. 3, 2013, which issued during the prosecution of U.S. Appl. No. 12/774,254.

An Office Action dated Apr. 19, 2012, which issued during the prosecution of U.S. Appl. No. 12/774,254.

An Office Action dated Jan. 29, 2013, which issued during the prosecution of U.S. Appl. No. 12/602,787.

A Supplementary European Search Report dated Dec. 14, 2012, which issued during the prosecution of European Patent Application No. 06766171.

An International Search Report dated Dec. 5, 2011, which issued during the prosecution of Applicant's PCT/IL11/00356.

Logan, "Percutaneous Mitral Valve Therapy", RN Foundation for Cardiovascular Medicine, La Jolla, pp. 20-22, 2008.

Davos, "The Effect of Baroreceptor Activity on Cardiovascular Regulation"; Hellenic j. Cardiol; 43:145-155; 2002.

Office action dated Oct. 21, 2014 for U.S. Appl. No. 13/116,370.

* cited by examiner

ELLIPTICAL ELEMENT FOR BLOOD PRESSURE REDUCTION

CROSS-REFERENCES TO RELATED APPLICATIONS

The present patent application is a continuation-in-part of International Patent Application PCT/IL2006/000856 to Gross (WO 07/013065), filed Jul. 25, 2006, entitled, "Electrical stimulation of blood vessels," which claims the benefit of (a) U.S. Provisional Application 60/702,491, filed Jul. 25, 2005, entitled, "Electrical stimulation of blood vessels," and (b) U.S. Provisional Application 60/721,728, filed Sep. 28, 2005, entitled, "Electrical stimulation of blood vessels." All of the above applications are incorporated herein by reference.

FIELD OF THE INVENTION

The present invention generally relates to implanted medical apparatus. Specifically, the present invention relates to apparatus and methods for reducing blood pressure.

BACKGROUND OF THE INVENTION

Hypertension is a condition from which many people suffer. It describes a constant state of elevated blood pressure which can be caused by a number of factors, for example, genetics, obesity or diet. Baroreceptors located in the walls of blood vessels act to regulate blood pressure. They do so by sending information to the central nervous system (CNS) regarding the extent to which the blood vessel walls are stretched by the pressure of the blood flowing therethrough. In response to these signals, the CNS adjusts certain parameters so as to maintain a stable blood pressure.

US Patent Application Publication 2003/0060858 to Kieval et al., which is incorporated herein by reference, describes devices, systems and methods by which the blood pressure, nervous system activity, and neurohormonal activity may be selectively and controllably reduced by activating baroreceptors. A baroreceptor activation device is positioned near a baroreceptor, for example a baroreceptor in the carotid sinus. A control system may be used to modulate the baroreceptor activation device. The control system may utilize an algorithm defining a stimulus regimen which promotes long term efficacy and reduces power requirements/consumption.

US Patent Application Publication 2005/0154418 to Kieval et al., which is incorporated herein by reference, describes systems and methods to provide baroreflex activation to treat or reduce pain and/or to cause or enhance sedation or sleep. Methods involve activating the baroreflex system to provide pain reduction, sedation, improved sleep or some combination thereof. Systems include at least one baroreflex activation device, at least one sensor for sensing physiological activity of the patient, and a processor coupled with the baroreflex activation device(s) and the sensor(s) for processing sensed data received from the sensor and for activating the baroreflex activation device. In some embodiments, the system is described as being fully implantable within a patient, such as in an intravascular, extravascular or intramural location.

US Patent Application Publication 2006/0074453 to Kieval et al., which is incorporated herein by reference, describes a method for treating heart failure in a patient which involves activating a baroreflex system of the patient with at least one baroreflex activation device and resynchronizing the patient's heart with a cardiac resynchronization device. Activating the baroreflex system and resynchronizing the heart may be performed simultaneously or sequentially, in various embodiments. In some embodiments, one or more patient conditions are sensed and such condition(s) may be used for setting and/or modifying the baroreflex activation and/or heart resynchronization. A device for treating heart failure includes a baroreflex activation member coupled with a cardiac resynchronization member. Some embodiments further include one or more sensors and a processor. In some embodiments, the device is fully implantable.

US Patent Application Publication 2005/0027346 to Arkusz et al., which is incorporated herein by reference, describes a tubular vascular stent graft with a passively pulsating midsection where the difference between the cross-sectional areas of the lumen under the systolic and diastolic pressures after the implantation is 10% or more. The pulsating stent graft accumulates blood during the systolic pressure wave thus lowering the peak value of the tugging force at the proximal attachment site.

PCT Publication WO 03/076008 to Shalev, which is incorporated herein by reference, describes an implantable device which uses the carotid baroreflex in order to control systemic blood pressure. The implant includes sampling and pulse stimulation electrodes preferably located on the carotid sinus nerve branch of the glossopharyngeal nerve, adjacent and distal to the carotid sinus baroreceptors. The stimulators have an external control unit, which communicates with the implant for determining appropriate operational parameters, and for retrieving telemetry information from the device's data bank. Typically, two internal devices are implanted, one at each side of the patient's neck.

PCT Publication WO 04/073484 to Gross et al., which is incorporated herein by reference, describes apparatus which includes an inflatable bladder, adapted to be coupled to a blood vessel of a subject carrying oxygenated blood, such that an interior of the bladder is in fluid communication with the blood. The apparatus also includes a piston in mechanical communication with the bladder; a motor, adapted to synchronize contraction and expansion of the bladder with a cardiac cycle of the subject by applying a motor force to the piston; and a spring, adapted to apply a spring force to the piston. In some embodiments of the invention, a counterpulsation system comprises one or more springs, which are adapted to be inserted into an artery of a subject, such as a descending aorta. Typically, each of the springs is planar, i.e., flat rather than helical, and has a generally sinusoidal shape. For applications comprising more than one spring, the plurality of springs are arranged in substantially a single plane. The counterpulsation system causes the artery to have a cross-sectional area during diastole that is less than the cross-sectional area would be during diastole without use of the counterpulsation system. For example, the counterpulsation system may cause the artery to have a cross-sectional shape during diastole that generally resembles an ellipse. Use of the counterpulsation system is described as thus typically increasing diastolic blood pressure and decreasing systolic blood pressure, thereby providing counterpulsation treatment to the circulation of the subject.

CVRx (Minneapolis, Minn.) manufactures the CVRx® Rheos Baroreflex Hypertension Therapy System, an implantable medical device for treating patients with high blood pressure. The product, which is under clinical investigation, works by electrically activating the baroreceptors, the sensors that regulate blood pressure. These baroreceptors are located on the carotid artery and in the carotid sinus. CVRx states that when the baroreceptors are activated by the Rheos System, signals are sent to the central nervous system and interpreted as a rise in blood pressure. The brain works to counteract this perceived rise in blood pressure by sending signals to other parts of the body to reduce blood pressure, including the heart, kidneys and blood vessels.

The following patents and patent applications, which are incorporated herein by reference, may be of interest:

US Patent Application Publication 2005/0033407 to Weber et al.
European Patent 0,791,341 to Demeyere et al.
PCT Publication WO 06/032902 to Caro et al.
U.S. Pat. No. 7,044,981 to Liu et al.
US Patent Application Publication 2005/0203610 to Tzeng
US Patent Application Publication 2004/0193092 to Deal
U.S. Pat. No. 6,575,994 to Marin et al.
US Patent Application Publication 2005/0232965 to Falotico
US Patent Application Publication 2004/0106976 to Bailey et al.
U.S. Pat. No. 4,938,766 to Jarvik
U.S. Pat. No. 4,201,219 to Bozal Gonzalez
U.S. Pat. No. 3,650,277 to Sjostrand et al.
U.S. Pat. No. 4,791,931 to Slate

SUMMARY OF THE INVENTION

As people age, their blood vessels become more rigid, and, as a result, the baroreceptor response to changes in blood pressure decreases. The CNS interprets the low baroreceptor response as resulting from a low blood pressure, and responds by increasing blood pressure. This phenomenon can cause or exacerbate hypertension. Embodiments of the present invention reduce hypertension by increasing the changes in shape of given arteries during the cardiac cycle. Doing so increases the baroreceptor signaling to the CNS, and the CNS interprets the increased baroreceptor signaling as having resulted from elevated blood pressure. In response, the CNS acts to lower blood pressure.

In some embodiments of the present invention, an element having an elliptical or other non-circular cross-section is placed near a baroreceptor in a blood vessel of a subject who has hypertension. The elliptical element changes the shape of the blood vessel such that the blood vessel is generally elliptical during diastole and less elliptical (e.g., generally circular) during systole.

In some embodiments of the invention, the non-circular element comprises a stent. Alternatively or additionally, the non-circular element comprises a ring, or a plurality of rings. For some applications, the one or more rings are used as the non-circular element in order to reduce the total surface contact between the element and the blood vessel, which, in turn, limits fibrosis between the element and the blood vessel. Alternatively, as when the element comprises a stent, the contact surface area is not necessarily minimized, and the one or more rings are used as the non-circular element for a different purpose.

In an embodiment, the ring is flexible and flexes in coordination with the cardiac cycle of the subject. In a further embodiment, a control unit is configured to detect the real-time blood pressure of the subject and to drive current, via the element, toward the baroreceptor, responsively to the detected blood pressure. Alternatively or additionally, the apparatus comprises a dedicated electrode, and current is driven toward the baroreceptor, via the dedicated electrode, responsively to the detected blood pressure.

In an embodiment, the cross-section of the ring is altered in response to the detection of real-time blood pressure of the subject. For example, if the blood pressure of the subject increases as a result of the subject undergoing a stressful experience, a blood pressure detector detects the increase. The detected increase in blood pressure results in the eccentricity of the ring being increased.

In some patients, the baroreceptor adapts to the presence of the ring within the blood vessel, and reverts toward its original firing rate. In some embodiments of the invention, the eccentricity of the ring is modified periodically, in response to measurements of resting blood pressure of the subject. For example, a balloon may be transcatheterally inserted into the inside of the ring. The balloon is inflated to modify the cross-section of the ring.

In some embodiments, an embolic protection device is inserted into the blood vessel during the implantation of the non-circular element. Typically, the embolic protection device comprises a mesh, and the mesh is placed distal to the non-circular element. The mesh is typically inserted into the blood vessel transcatheterally.

There is therefore provided, in accordance with an embodiment of the invention, apparatus for treating hypertension of a subject, including an implantable element which has a non-circular shape and which is configured to reduce the hypertension by facilitating an assumption of a non-circular shape by a blood vessel in a vicinity of a baroreceptor of the subject, during diastole of the subject.

In an embodiment, the element includes a non-circular stent.

In an embodiment, the element includes a single non-circular ring.

In an embodiment, the element includes a plurality of non-circular rings.

In an embodiment, the element includes a plurality of non-circular rings which are not connected to each other.

In an embodiment, the element includes a plurality of non-circular rings which are not rigidly connected to each other.

In an embodiment, the element is rigid.

In an embodiment, the apparatus includes a control unit configured to detect real-time blood pressure of the subject.

In an embodiment, the control unit is configured to be implantable in a body of the subject.

In an embodiment, the control unit is configured to drive current, via the element, toward the baroreceptor, in response to the detected blood pressure.

In an embodiment, the apparatus includes an electrode, and the control unit is configured to drive current, via the electrode, toward the baroreceptor, in response to the detected blood pressure.

In an embodiment, the control unit is configured to change the cross-section of the element in response to the detected blood pressure.

In an embodiment, the element includes a plurality of rings which are coupled to each other.

In an embodiment, the apparatus includes a single rod, and the rings are coupled to each other by the single rod.

In an embodiment, the apparatus includes exactly two rods, and the rings are coupled to each other by the exactly two rods.

In an embodiment, the apparatus includes three or more rods, and the rings are coupled to each other by the three or more rods.

In an embodiment, the element includes two rings which are coupled to each other and which are separated from each other by a distance that is between 5 mm and 20 mm.

In an embodiment, the element includes two rings which are coupled to each other and which are separated from each other by a distance that is between 20 mm and 50 mm.

In an embodiment, the element is flexible.

In an embodiment, the element is configured to flex in coordination with a cardiac cycle of the subject.

In an embodiment, the element is configured to flex passively in coordination with the cardiac cycle of the subject.

In an embodiment, the apparatus includes a control unit configured to detect the cardiac cycle of the subject and to flex the element in coordination with the cardiac cycle.

In an embodiment, the apparatus includes a shaping element configured to shape the non-circular element while the non-circular element is in the blood vessel.

In an embodiment, the shaping element includes a balloon.

In an embodiment, the shaping element includes an elliptical balloon.

In an embodiment, the apparatus includes an embolic protection device configured to capture emboli during implanting of the element.

In an embodiment, the embolic protection device includes a mesh.

There is additionally provided, in accordance with an embodiment of the invention, a method for reducing hypertension of a subject, including:

coupling an element having a non-circular cross-section to a blood vessel of the subject in a vicinity of a baroreceptor of the subject, by implanting the element; and reducing the hypertension by facilitating, with the element, an assumption of a non-circular shape by the blood vessel in the vicinity, during diastole of the subject.

In an embodiment, implanting the element includes implanting in separate implantation steps, at respective longitudinal sites of the blood vessel in the vicinity of the baroreceptor, a plurality of rings having non-circular cross-sections.

In an embodiment, implanting the element includes implanting, at respective longitudinal sites of the blood vessel in the vicinity of the baroreceptor, a plurality of rings which are coupled to each other, the rings having non-circular cross-sections.

In an embodiment, implanting the element includes implanting the element during minimally-invasive surgery.

In an embodiment, implanting the element includes placing a stent inside the blood vessel on one side of the baroreceptor, the stent having a non-circular cross-section.

In an embodiment, implanting the element includes placing a ring inside the blood vessel on one side of the baroreceptor, the ring having a non-circular cross-section.

In an embodiment, the method includes detecting blood pressure of the subject and changing the cross-section of the non-circular element in response to the detected blood pressure.

In an embodiment, detecting the blood pressure includes detecting the blood pressure of the subject more frequently than once a week.

In an embodiment, detecting the blood pressure includes detecting the blood pressure of the subject less frequently than once a week.

In an embodiment, detecting the blood pressure includes detecting real time blood pressure of the subject, and changing the cross-section of the element includes changing the cross-section of the element in response to the detected real time blood pressure.

In an embodiment, detecting the blood pressure includes detecting resting blood pressure of the subject, and changing the cross-section of the element includes changing the cross-section of the element in response to the detected resting blood pressure.

In an embodiment, changing the cross-section of the element includes expanding a balloon within the element.

In an embodiment, changing the cross-section of the element includes expanding an elliptical balloon within the element.

In an embodiment, changing the cross-section of the element includes driving a current toward the element.

In an embodiment, the element includes first and second rings having non-circular cross-sections, and implanting the element includes implanting the first ring on one side of the baroreceptor and implanting the second ring on another side of the baroreceptor.

In an embodiment, implanting the first ring and the second ring includes implanting the first and second rings, the rings not being connected to each other.

In an embodiment, implanting the first ring and the second ring includes implanting the first and second rings, the rings not being rigidly connected to each other.

In an embodiment, implanting the first ring and the second ring includes implanting the first and second rings, the rings being coupled to each other.

In an embodiment, implanting the first ring and the second ring includes implanting the first and second rings at a longitudinal distance from each other that is between 5 mm and 20 mm.

In an embodiment, implanting the first ring and the second ring includes implanting the first and second rings at a longitudinal distance from each other that is between 20 mm and 50 mm.

There is additionally provided, in accordance with an embodiment of the invention, a method for reducing hypertension of a subject, including:

coupling a ring having a non-circular cross-section to a blood vessel of the subject in a vicinity of a baroreceptor of the subject, by implanting the ring; and reducing the hypertension by facilitating, with the ring, an assumption of a non-circular shape by the blood vessel in the vicinity, during diastole of the subject.

In some embodiments, implanting the ring includes implanting the ring during minimally-invasive surgery.

In some embodiments, the ring includes a rigid ring, and implanting the ring includes implanting the rigid ring.

In some embodiments, the method includes detecting blood pressure of the subject and changing the cross-section of the non-circular ring in response to the detected blood pressure.

In some embodiments, detecting the blood pressure includes detecting the blood pressure of the subject more frequently than once a week.

In some embodiments, detecting the blood pressure includes detecting the blood pressure of the subject less frequently than once a week.

In some embodiments, detecting the blood pressure includes detecting real time blood pressure of the subject, and changing the cross-section of the ring includes changing the cross-section of the ring in response to the detected real time blood pressure.

In some embodiments, detecting the blood pressure includes detecting resting blood pressure of the subject, and changing the cross-section of the ring includes changing the cross-section of the ring in response to the detected resting blood pressure.

In some embodiments, changing the cross-section of the ring includes expanding a balloon within the ring.

In some embodiments, changing the cross-section of the ring includes expanding an elliptical balloon within the ring.

In some embodiments, changing the cross-section of the ring includes driving a current toward the ring.

In some embodiments, the ring includes a flexible ring, and implanting the ring includes implanting the flexible ring.

In some embodiments, the ring is configured to flex in response to a cardiac cycle of the subject, and implanting the ring includes implanting the ring that is configured to flex in response to the cardiac cycle.

In some embodiments, the ring is configured to flex passively in coordination with the cardiac cycle of the subject, and implanting the ring includes implanting the ring that is configured to flex passively in coordination with the cardiac cycle.

In some embodiments, the ring is coupled to a control unit, the control unit being configured to detect the cardiac cycle of the subject and to flex the ring in coordination with the cardiac cycle, and implanting the ring includes implanting the ring that is coupled to the control unit.

In some embodiments, the method includes detecting real-time blood pressure of the subject and driving a current toward the baroreceptor responsively to the detected blood pressure.

In some embodiments, driving the current includes driving the current via the ring.

In some embodiments, driving the current includes driving the current via an electrode.

In some embodiments, the method includes providing embolic protection during the implanting.

In some embodiments, providing the embolic protection includes placing a mesh within the blood vessel.

There is additionally provided, in accordance with an embodiment of the invention, apparatus for treating hypertension of a subject, including an implantable ring which has a non-circular shape and which is configured to reduce the hypertension by facilitating an assumption of a non-circular shape by a blood vessel in a vicinity of a baroreceptor of the subject, during diastole of the subject.

In some embodiments, the ring is rigid.

In some embodiments, the apparatus includes a control unit configured to detect real-time blood pressure of the subject.

In some embodiments, the control unit is configured to be implantable in a body of the subject.

In some embodiments, the control unit is configured to drive current, via the ring, toward the baroreceptor, in response to the detected blood pressure.

In some embodiments, the apparatus includes an electrode, wherein the control unit is configured to drive current, via the electrode, toward the baroreceptor, in response to the detected blood pressure.

In some embodiments, the control unit is configured to change the cross-section of the ring in response to the detected blood pressure.

In some embodiments, the ring is flexible.

In some embodiments, the ring is configured to flex in coordination with a cardiac cycle of the subject.

In some embodiments, the ring is configured to flex passively in coordination with the cardiac cycle of the subject.

In some embodiments, the apparatus includes a control unit configured to detect the cardiac cycle of the subject and to flex the ring in coordination with the cardiac cycle.

In some embodiments, the apparatus includes a shaping element configured to shape the non-circular ring while the non-circular ring is in the blood vessel.

In some embodiments, the shaping element includes a balloon.

In some embodiments, the shaping element includes an elliptical balloon.

In some embodiments, the apparatus includes an embolic protection device configured to capture emboli during implanting of the ring.

In some embodiments, the embolic protection device includes a mesh.

The present invention will be more fully understood from the following detailed description of embodiments thereof, taken together with the drawings, in which:

DETAILED DESCRIPTION OF EMBODIMENTS

Figure 1A:
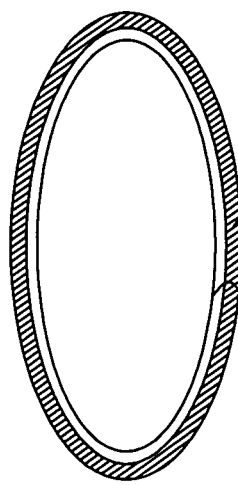
FIGS. 1A and 1B are schematic illustrations of a non-circular rigid implant element inside a blood vessel during diastole and during systole, respectively, in accordance with an embodiment of the present invention.
Figure 1B:
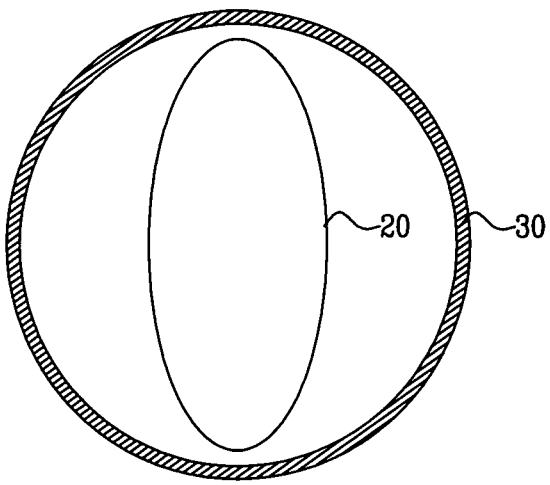

Reference is now made to FIGS. 1A and 1B, which are schematic illustrations of a non-circular implant element 20 disposed within a blood vessel 30 of a subject, in accordance with an embodiment of the invention. Typically, the element is implanted into the aorta or the carotid artery of the subject. FIG. 1A shows the blood vessel during diastole and FIG. 1B shows the blood vessel during systole. Typically, the element includes one or more elliptical rigid rings, and/or an elliptical stent. The element is placed within the blood vessel in the vicinity of a baroreceptor and causes an increase in the change in shape which the blood vessel would in any case undergo during the cardiac cycle.

In some embodiments, the element is placed as close as possible to the baroreceptor, e.g., within 1 cm or 2 cm of the baroreceptor. The implanting is typically performed during minimally-invasive surgery, e.g., using a transcatheter approach.

Figure 1C:
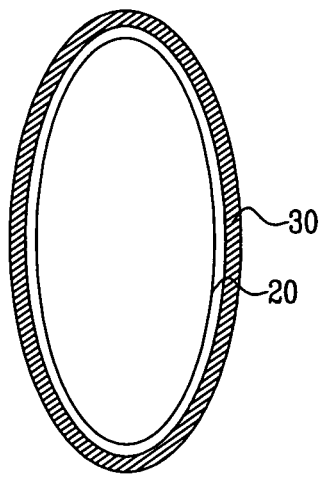
FIGS. 1C and 1D are schematic illustrations of a non-circular flexible implant element inside a blood vessel during diastole and during systole, respectively, in accordance with another embodiment of the present invention.
Figure 1D:
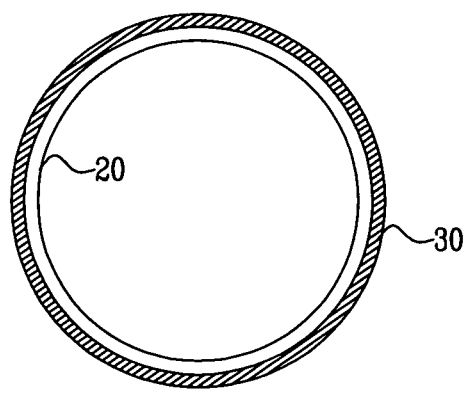

Reference is now made to FIGS. 1C and 1D, which are schematic illustrations of non-circular element 20, in accordance with another embodiment of the present invention. In some embodiments (as shown), non-circular element 20 is flexible and flexes passively in coordination with the cardiac cycle. Blood vessel 30 changes the shape of element 20 from being non-circular during diastole (FIG. 1C), to being more circular during systole (FIG. 1D). For example, element 20 may be generally circular during systole, or generally elliptical, with lower eccentricity than during diastole. In all other aspects element 20 is generally the same as described hereinabove.

Figure 2:
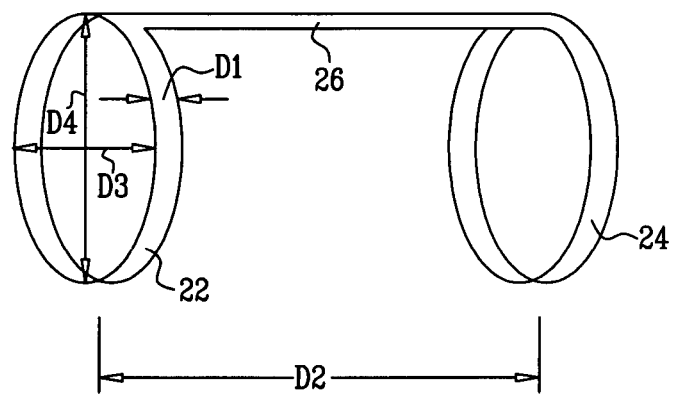
FIG. 2 is a schematic illustration of two non-circular rings which are coupled to each other, in accordance with an embodiment of the invention.
Figure 3:
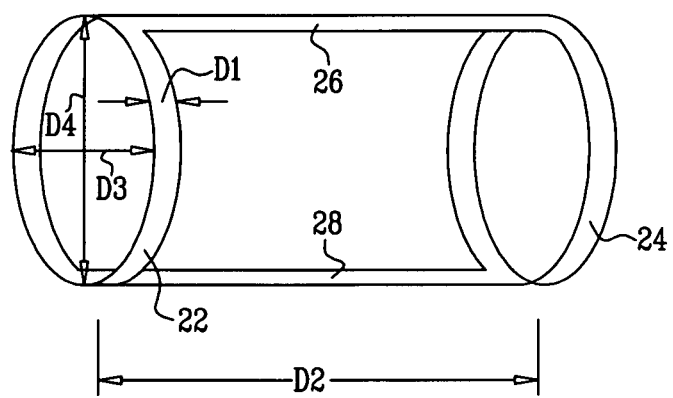
FIG. 3 is a schematic illustration of two non-circular rings which are coupled to each other, in accordance with another embodiment of the invention.

Reference is now made to FIGS. 2 and 3, which are schematic illustrations of implant element 20, comprising two non-circular rings 22 and 24, which are coupled to each other by a single rod 26 (FIG. 2) or two or more rods 26 and 28 (FIG. 3), in accordance with respective embodiments of the invention. Typically, the width D1 of each of the rings is between 2 mm and 6 mm, e.g., 4 mm, and the rings are implanted at a longitudinal separation D2 from each other, along the blood vessel, which is between about 5 mm and 20 mm, or between about 20 mm and 50 mm. During diastole, the ratio of length D4 of the major axis of the ellipse to length D3 of the minor axis is typically between 1.5:1 and 2.5:1, e.g., 2:1. For some applications, the rings are implanted such that one ring is disposed within the blood vessel on one side of the baroreceptor and the second ring is disposed within the blood vessel on the other side of the baroreceptor. In some embodiments, the two rings are not connected to each other and are implanted in separate implantation steps. In alternative embodiments, the two rings are coupled to each other by three or more rods.

Figure 4A:
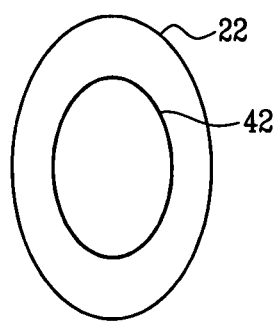
FIGS. 4A and 4B are schematic illustrations of a balloon inside a non-circular ring, the balloon in deflated and inflated states thereof, respectively, in accordance with an embodiment of the present invention.
Figure 4B:
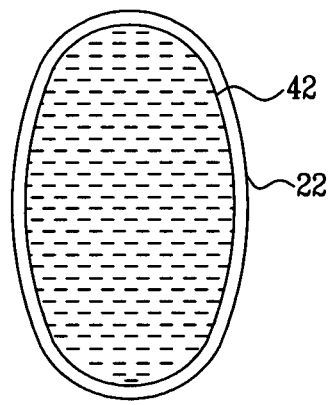

Reference is now made to FIGS. 4A and 4B, which are schematic illustrations of a shaping balloon 42, inside non-circular ring 22, in accordance with an embodiment of the present invention. In FIG. 4A, the balloon is deflated, and in FIG. 4B, the balloon is inflated. In some patients, baroreceptors adapt to a ring being deployed within a blood vessel (as described herein) and revert toward their original firing rate. In an embodiment of the invention, periodic measurements are made of the subject's resting blood pressure. If the blood pressure of the subject has increased, the eccentricity of the cross-section of the ring is increased by inflation of shaping balloon 42. Typically, the balloon is inserted transcatheterally into the inside of the ring, and the balloon is inflated. The balloon expands and permanently increases the eccentricity of the cross-section of the implanted ring. Alternatively, if it is determined that the eccentricity of the ring is having too great an effect on resting blood pressure, the balloon is inflated in a manner to decrease eccentricity (e.g., by increasing the minor axis of the ring).

Figure 5A:
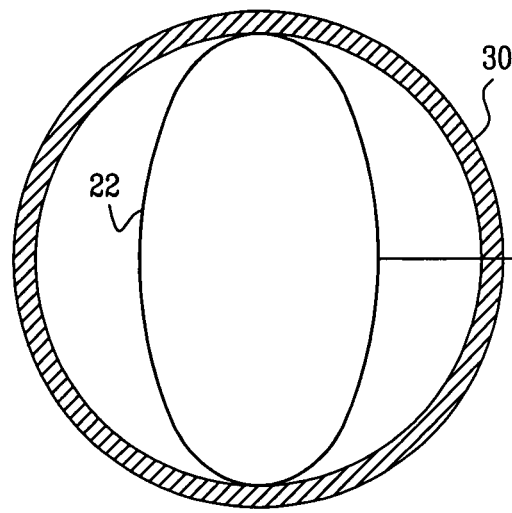
FIGS. 5A and 5B are schematic illustrations of apparatus for increasing the rate of firing of a baroreceptor, in accordance with respective embodiments of the invention.
Figure 5B:
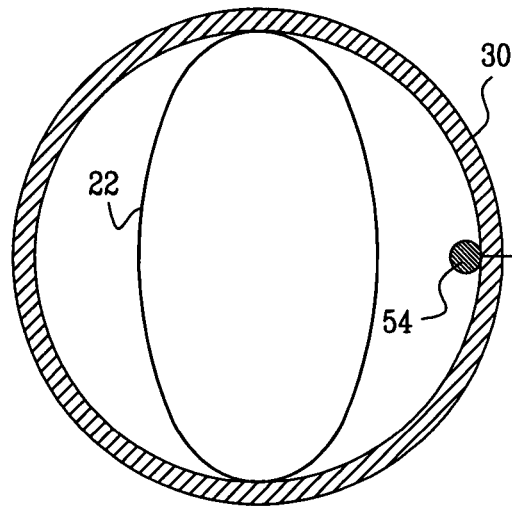

Reference is now made to FIGS. 5A and 5B, which are schematic illustrations of apparatus for increasing the rate of firing of a baroreceptor, in accordance with respective embodiments of the invention. The apparatus comprises elliptical ring 22, which is implanted in blood vessel 30, and control unit 52. In FIGS. 5A and 5B, blood vessel 30 is shown during systole. In FIG. 5A the control unit is coupled to the ring, and in FIG. 5B, the control unit is coupled to an electrode 54. In some embodiments, the control unit is configured to detect real-time blood pressure of the subject. The control unit is configured to drive a current into the blood vessel to excite the baroreceptor, in a transient manner, in response to real-time blood pressure measurements. For example, the control unit may detect a transient increase in blood pressure as a result of the subject undergoing a stressful experience. In response, the control unit excites the baroreceptor. The current is typically driven into the blood vessel via the ring (FIG. 5A) and/or via the electrode (FIG. 5B). Alternatively, or additionally, the control unit is configured to transiently modulate the eccentricity of the ring in response to the real-time blood pressure measurements. For example, the ring may comprise mechanical deforming elements (e.g., piezoelectric elements), and the control unit actuates the deforming elements to transiently alter the eccentricity of the ring.

In some embodiments, the ring is flexible, and the control unit is configured to detect the cardiac cycle of the subject and to flex the ring in coordination with the cardiac cycle, to enhance baroreceptor firing and blood pressure reduction.

Figure 6:
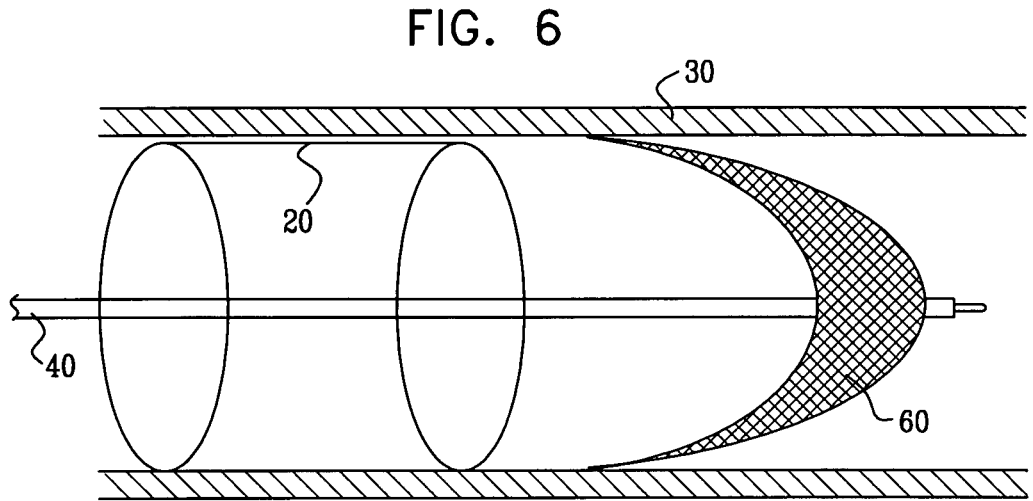
FIG. 6 is a schematic illustration of an implant element having embolic protection, in accordance with an embodiment of the invention.

Reference is now made to FIG. 6, which is a schematic illustration of an embolic protection device 60 disposed within the blood vessel during implantation of element 20, in accordance with an embodiment of the present invention. The implant element and the embolic protection device are placed in blood vessel 30 in the vicinity of a baroreceptor. Typically, the embolic protection device comprises a mesh. During the implanting of the implant element, the embolic protection device is inserted into the blood vessel distal to the implant element. Embolic protection device 60 is typically inserted into the blood vessel via a catheter 40. The protection device prevents embolisms, caused by the implanting of the implant element, from occluding blood vessels of the subject. Following implantation of element 20, embolic protection device 60 is removed.

It is to be understood that use of a non-circular plurality of rings is described herein by way of illustration and not limitation, and that the scope of the present invention includes the use of a plurality of rings that are circular in cross-section.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A method of reducing hypertension of a subject, comprising:
   coupling a flexible element having a non-circular cross-section to a carotid artery of the subject in a vicinity of a baroreceptor of the subject, by implanting the flexible element within the carotid artery, the flexible element being configured to flex passively in coordination with the cardiac cycle; and
   facilitating, with the flexible element, an assumption of a non-circular cross-sectional shape by the carotid artery in the vicinity that is less circular than a shape of the carotid artery in the vicinity when the element is not coupled to the carotid artery, wherein passive flexure of the flexible element in coordination with the cardiac cycle reduces hypertension of the subject.

2. The method according to claim 1, further comprising facilitating, with the element, an assumption of a cross-sectional shape by the carotid artery in the vicinity, during diastole of the subject, that is less circular than a shape of the carotid artery in the vicinity, during systole of the subject.

3. The method according to claim 2, wherein implanting the element comprises implanting a stent which has a non-circular cross-section.

4. The method according to claim 2, wherein implanting the element comprises placing the element inside the carotid artery on a side of the baroreceptor selected from the group consisting of: an upstream side, and a downstream side.

5. The method according to claim 2, wherein the element includes a spring and implanting the element comprises coupling the spring to the carotid artery.

6. The method according to claim 2, wherein implanting the element comprises coupling two elements to the carotid artery at a longitudinal separation from each other, the elements having non-circular cross-sections.

7. The method according to claim 6, wherein coupling the two elements to the carotid artery comprises longitudinally spacing the two elements by between 5 mm and 20 mm.

8. The method according to claim 2, wherein the element includes first and second elements having non-circular cross-sections, and wherein implanting the elements comprises implanting the first element on a first side of the baroreceptor and implanting the second element on a second side of the baroreceptor, the first and second sides being respective sides selected from the group consisting of: an upstream side and a downstream side.

9. The method according to claim 8, wherein implanting the first element and the second element comprises implanting the first and second elements, the elements being coupled to each other.

* * * * *